(12) United States Patent
Aoyagi et al.

(10) Patent No.: US 7,206,621 B2
(45) Date of Patent: Apr. 17, 2007

(54) PULSE OXIMETER

(75) Inventors: Takuo Aoyagi, Tokyo (JP); Masayoshi Fuse, Tokyo (JP); Naoki Kobayashi, Tokyo (JP); Teiji Ukawa, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 249 days.

(21) Appl. No.: 10/927,016

(22) Filed: Aug. 27, 2004

(65) Prior Publication Data
US 2005/0049469 A1    Mar. 3, 2005

(30) Foreign Application Priority Data
Aug. 27, 2003    (JP)    ............ P2003-302516

(51) Int. Cl.
*A61B 5/00*    (2006.01)
(52) U.S. Cl. .................... 600/323; 600/336
(58) Field of Classification Search ............. 600/323, 600/336
See application file for complete search history.

(56) References Cited

U.S. PATENT DOCUMENTS

| | | | | |
|---|---|---|---|---|
| 3,638,640 | A | * | 2/1972 | Shaw .................. 600/323 |
| 4,114,604 | A | * | 9/1978 | Shaw et al. ............ 600/339 |
| 5,692,503 | A | * | 12/1997 | Kuenstner ............. 600/322 |
| 5,720,284 | A | | 2/1998 | Aoyagi et al. |
| 5,766,125 | A | | 6/1998 | Aoyagi et al. |
| 6,195,574 | B1 | * | 2/2001 | Kumar et al. ........... 600/323 |
| 6,230,035 | B1 | | 5/2001 | Aoyagi et al. |

FOREIGN PATENT DOCUMENTS

| | | |
|---|---|---|
| JP | 5-88609 B2 | 12/1993 |
| JP | 8-10245 A | 1/1996 |
| JP | 8-322822 A | 12/1996 |
| JP | 11-216133 A | 8/1999 |
| JP | 2000-83933 A | 3/2000 |

OTHER PUBLICATIONS

Hewlett Packard model 47201 A ear oximeter; Sep. 1975; pp. 1-8; USA.

* cited by examiner

*Primary Examiner*—Eric F. Winakur
*Assistant Examiner*—Jack Lin
(74) *Attorney, Agent, or Firm*—Sughrue Mion, PLLC

(57) ABSTRACT

In a pulse oximeter for obtaining an oxygen saturation in a blood, a light emitter irradiates a living tissue with light beams having five different wavelengths. A light receiver receives respective light beams reflected from or transmitted through the living tissue, and converts the received light beams to electric signals. A first calculator calculates five attenuation changes of the living tissue based on fluctuations of the respective electric signals. A second calculator calculates at least four attenuation change ratios from the five attenuation changes. Each of the attenuation change ratios is defined by a ratio between any two of the five attenuation changes. A third calculator calculates the oxygen saturation based on the attenuation change ratios, while taking an oxygen saturation of arterial blood, an oxygen saturation of venous blood, a ratio between changes in arterial blood and venous blood, and a tissue term as four unknown values.

4 Claims, 7 Drawing Sheets

PULSE OXIMETER

BACKGROUND OF THE INVENTION

The present invention relates to a pulse oximeter which can measure an oxygen saturation of arterial blood continuously and non-invasively by utilization of variations in the volume of arterial blood by pulsation.

A pulse oximeter has hitherto been widely known as an apparatus which measures an oxygen saturation of blood; more specifically, a concentration ratio of oxyhemoglobin to a sum of oxyhemoglobin and deoxyhemoglobin. Japanese Patent Publication No. 5-88609B discloses an apparatus for determining concentrations of constituents of blood with high precision without being affected by pure tissue whose thickness varies due to pulsation of blood.

More specifically, this publication discloses an apparatus for determining concentrations of constituents of blood comprising: a light emitter which irradiates a living tissue with light beams of N different wavelengths; a light receiver which receives light originated from the light emitter and then reflected from or transmitted through a living tissue; a first circuit which detects an attenuation change at the living tissue based on output signals from the light receiver for each of the N wavelengths; a second circuit which calculates N−1 attenuation change ratios between different wavelengths, in accordance with detection signals pertaining to the N different wavelengths output from the first circuit; and a third circuit for calculating which calculates relative concentrations of N−1 constituents of blood, through use of arithmetic equations determined by solving simultaneous equations with N−1 unknowns in connection with concentrations of constituents of blood, on the basis of values of attenuation change ratios output from the second circuit. This calculation is based on the assumption that attenuation changes in the living tissue stem from changes in the thickness of blood and thickness of pure tissue which does not include blood.

In the above apparatus, the second circuit enables calculation of a ratio between N−1 pulsation changes in different wavelengths when the second circuit receives signals output from the first circuit. The third circuit performs computation by substituting actually-measured values of ratios of pulsation changes and respective coefficient values into an equation for determining relative concentrations of N−1 constituents of blood. The equation is obtained by solving simultaneous equations pertaining to N−1 pulsation change ratios that also take into consideration the influence of pulsation of pure tissue. Accordingly, concentrations (relative concentrations) of N−1 constituents of blood can be measured with high precision and without being influenced by pulsation of pure tissue.

Meanwhile, when body motion occurs during measurement of concentrations of constituents of blood by a pulse oximeter, artifacts are superposed on the transmitted light. When the artifacts stemming from such body motion arm large, difficulty is encountered in removing the artifacts by correcting pulse waveforms, or the like. Japanese Patent Publication No. 11-216133A discloses a pulse oximeter capable of performing high-precision measurement without being influenced by the artifacts stemming from body motion even when the artifacts are large.

More specifically, the pulse oximeter comprises: a light emitter which irradiates a living tissue with a plurality of light beams having different wavelengths; a photoelectric converter which converts a light beam transmitted through the living tissue into an electric signal for each of the wavelengths; a first detector which detects an attenuation change at the living tissue based on fluctuations of the signals output from the photoelectric converter for each of the wavelengths; a variable filter which receives the attenuation change for each of the wavelengths and allows to pass through a component having a prescribed frequency band; a band prescriber which prescribes the frequency band for the variable filter; and a second detector which determines an oxygen saturation in accordance with an output from the variable filter.

The apparatus disclosed in Japanese Patent Publication No. 5-88609B teaches that a plurality of light beams having different wavelengths to precisely measure concentrations of constituents of blood without being influenced by pure tissue whose thickness varies due to pulsation of blood. The influence of a term of the pure tissue can be eliminated by use of light beams of three different wavelengths during the measurement process, thereby enabling measurement of a relative concentration between oxyhemoglobin and deoxyhemoglobin, which are two constituents of blood.

The influence of a term of the pure tissue can be eliminated by use of light beams of four different wavelengths during the measurement process, as in the case of the above, thereby enabling precise measurement of relative concentrations between oxyhemoglobin, deoxyhemoglobin and another pigment, which are three constituents of blood. Furthermore, use of light beams of five different wavelengths enables measurement of relative concentrations between four constituents of blood including carboxyhemoglobin in addition to the above three constituents of blood measured by use of the four different light wavelengths.

However, this publication is silent about the influence of the artifacts stemming from body motion. Therefore, means for eliminating the influence of the artifacts is not disclosed at all.

Meanwhile, Japanese Patent Publication No. 11-216133A teaches means for eliminating the influence of the artifacts stemming from body motion. However, in a pulse oximeter disclosed in this publication, changes in the thickness of arterial blood and changes in the thickness of pure tissue, which are assumed to be causes of the aromas stemming from body motion, are regarded as negligible factors. Focus is paid to changes in the thickness of venous blood as the paramount cause, and measures are taken against the changes in the thickness of venous blood. In summary, this publication teaches a method and an apparatus for performing: a two-wavelength measurement which disregards changes in tissue thickness; and a three-wavelength measurement which takes into consideration changes in tissue thickness.

Accordingly, the most serious problem faced by a currently available pulse oximeter is the artifacts stemming from body motion. A primary method adopted as a countermeasure for avoiding the influence of the artifacts stemming from body motion is a statistical method. Specifically, reference is made to antecedent data and subsequent data in order to obtain a reliable measurement value at a certain point in time. Therefore, such a measurement entails a time delay and value smoothing. This is against the primary object of a pulse oximeter to detect anomalies in a patient at an early stage. That is, a function for eliminating the influence of artifacts is insufficient or involves inconveniences.

SUMMARY OF THE INVENTION

It is therefore an object of the invention to provide a pulse oximeter capable of measuring an oxygen saturation of arterial blood with high precision by using a deterministic method which is able to eliminate the aforementioned influence of artifacts stemming from body motion, as well as eliminating the time delay and the value smoothing.

In order to achieve the above object, according to the invention, there is provided a pulse oximeter for obtaining an oxygen saturation in a blood, comprising:

a light emitter, adapted to irradiate a living tissue with light beams having five different wavelengths;

a light receiver, adapted to receive respective light beams reflected from or transmitted through the living tissue, and to convert the received light beams to electric signals;

a first calculator, which calculates five attenuation changes of the living tissue based on fluctuations of the respective electric signals;

a second calculator, which calculates at least four attenuation change ratios from the five attenuation changes, each of the attenuation change ratios being defined by a ratio between any two of the five attenuation changes; and a third calculator, which calculates the oxygen saturation based on the attenuation change ratios, while taking an oxygen saturation of arterial blood, an oxygen saturation of venous blood, a ratio between changes in arterial blood and venous blood, and a tissue term as four unknown values.

With the above configuration, the influence of the pulsation when venous blood is being pulsated for some reason can be reliably eliminated, whereby an oxygen saturation of arterial blood can be measured with high precision and without involving the time delay or the value smoothing. Furthermore, even in a case where a pulse wave in a living tissue of a subject is so small that a pulse oximetry is not applicable, measurement of an oxygen saturation of arterial blood is enabled by forcibly effecting body motion against the living tissue by a vibration mechanism or the like, to thus generate artifacts on attenuation changes in light transmitted through the living tissue. Moreover, an oxygen saturation of venous blood can also be measured simultaneously with the oxygen saturation of arterial blood.

According to the invention, there is also provided a method of obtaining an oxygen saturation in a blood, comprising steps of:

irradiating a living tissue with light beams having five different wavelengths;

receiving respective light beams reflected from or transmitted through the living tissue;

converting the received light beams to electric signals;

calculating five attenuation changes of the living tissue based on fluctuations of the respective electric signals;

calculating at least four attenuation change ratios from the five attenuation changes, each of the attenuation change ratios being defined by a ratio between any two of the five attenuation changes; and calculating the oxygen saturation based on the attenuation change ratios, while taking an oxygen saturation of arterial blood, an oxygen saturation of venous blood, a ratio between changes in arterial blood and venous blood, and a tissue term as four unknown values.

The venous blood is pressed by the pulsation of the arterial blood, and inverse pulsation is thus presented. This fact contributes an increase of the SpO2 value. This increase should not be ignored in a case where the SaO2 value is almost 100%. Although there is a possibility that the SpO2 value exceeds 100%, the conventional two-wavelength type pulse oxymeter ignores the amount of the SpO2 value exceeding 100%. However, the contribution from the inversed pulsation of the venous blood should be removed to obtain an accurate SpO2 value. For example, an extremely immature baby would become blind due to retinopathy if the SaO2 value is too large, whereas the baby would become encephalopathy or die if the SaO2 value is too small. It is apparent that the detection of an accurate SpO2 value is so critical for the extremely immature baby.

According to the above configurations, since the contribution from the inversed pulsation of the venous blood can be removed by the five-length measurement, so that an accurate SpO2 value can be obtained especially in the case where the SaO2 value is almost 100%. Therefore, it is advantageous for the respiration monitoring of the extremely immature baby.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE INVENTION

One embodiment of the present invention will be described below in detail with reference to the accompanying drawings.

Figure 1:
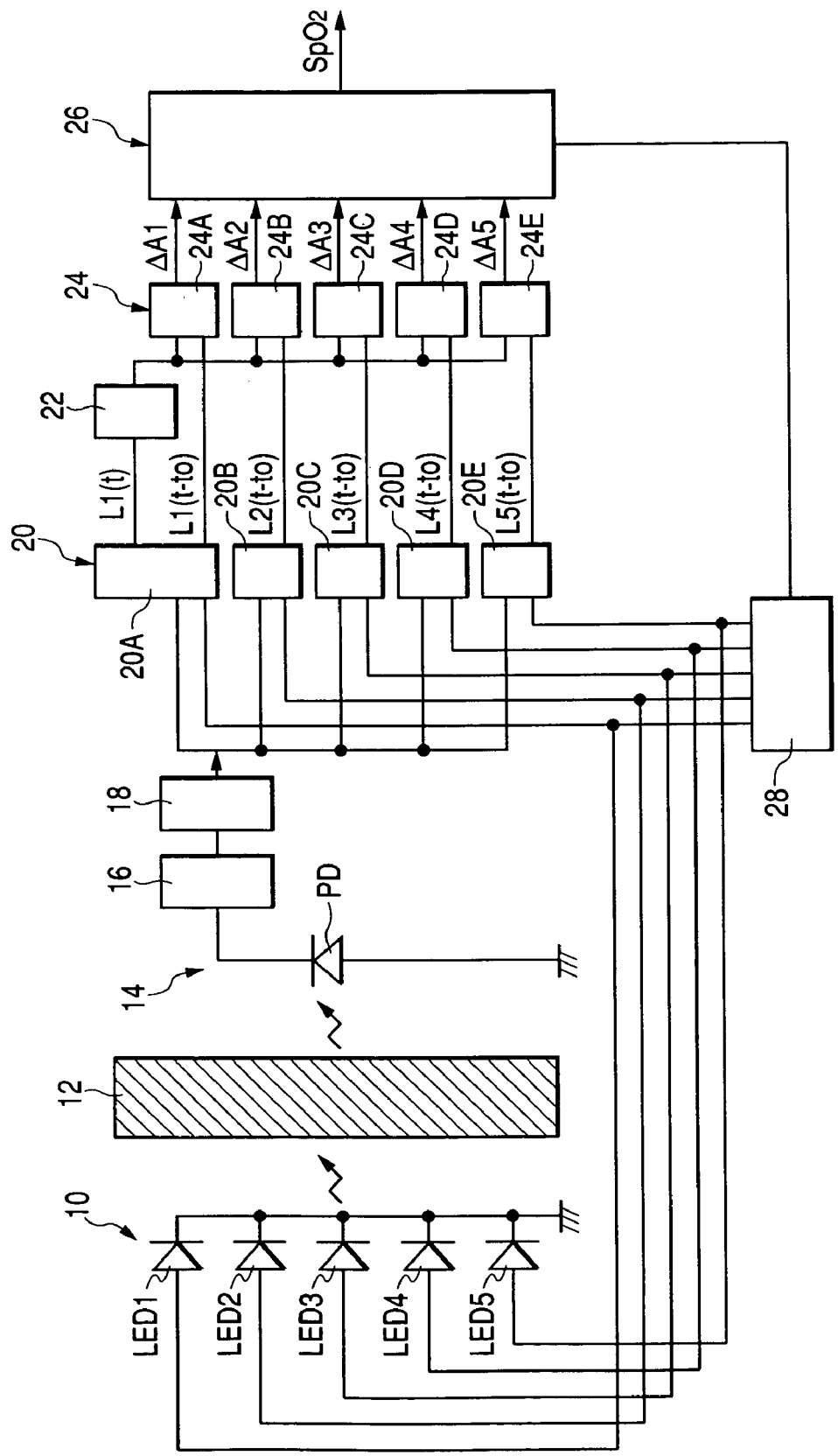
FIG. 1 is a block diagram showing an electric configuration of a pulse oximeter according to one embodiment of the present invention.

In a pulse oximeter shown in FIG. 1, a light emitter 10 includes five light emitting elements LED 1 to LED 5 for emitting light beams of five different wavelengths. The light beams emitted from the light emitter 10 are transmitted through a living tissue 12 and received by a light receiver 14 constituted by a light receiving element PD, a current-voltage converter 16, and an AD converter 18. The light receiver 14 outputs transmitted light signals for the respective wavelengths.

A storage unit 20 is formed from storage devices 20A to 20E which store the transmitted light signals of the respective wavelengths. A peak bottom detector 22 is configured to detect a peak value and a bottom value of changes in a transmitted light signal of one of the wavelengths, to thus output time points at which the peak value and the bottom value appear. A first calculator 24 is constituted by attenuation change calculators 24A to 24E which capture transmitted light signals of the respective wavelengths at the time points are obtained by the peak bottom detector 22 to calculate attenuation changes ΔAi (i=1, 2, 3, 4, 5) on the basis of the transmitted light signals.

A second calculator 26 is configured to calculate an oxygen saturation SpO2 on the basis of the attenuation changes ΔAi calculated by the respective attenuation change calculators 24A to 24E of the first calculator 24. More specifically, the second calculator 26 has the function of an attenuation change ratio calculator which calculates attenuation change ratios between the attenuation changes Φij=ΔAi/ΔAj (e.g., Φ12=ΔA1/ΔA2, Φ34=ΔA3/ΔA4, Φ51 = ΔA5/ΔA1, Φ23=ΔA2/ΔA3, Φ45=ΔA4/ΔA5) on the basis of the attenuation changes ΔAi; and the function of an oxygen saturation calculator which calculates the oxygen saturation of blood SpO$_2$ on the basis of the attenuation change ratios Φij by use of four unknown values consisting of: an oxygen saturation of arterial blood Sa; an oxygen saturation of venous blood Sv; a ratio V (=ΔDv/ΔDa) between changes in arterial blood ΔDa and changes in venous blood ΔDv; and a tissue term Wi.

A timer 28 is configured to generate a timing signal which is in conjunction with the operation of the second calculator 26, and controls a timing at which the respective light emitting elements LED 1 to LED 5 of the light emitter 10 are to be operated and a timing at which the transmitted light signals are to be stored in the respective storage devices 20A to 20E of the storage 20.

Next, operations of calculating oxygen saturation of arterial blood and venous blood in the pulse oximeter will be described.

The light emitting elements LED 1 to LED 5 of the light emitter 10 are caused to illuminate sequentially and alternately at different wavelengths λ1, λ2, λ3, λ4, and λ5 in accordance with the timing signal from the timer 28. As a result, light which has transmitted through the living tissue 12 is received at the light receiver 14. In response to the respective wavelengths of the light emitting elements LED 1 to LED 5, the respective transmitted light signals L1, L2, L3, L4, and L5 are stored in the respective storage devices 20A to 20E of the storage unit 20 in accordance with the timing signal from the timer 28. Meanwhile, the storage devices 20A to 20E store data pertaining to outputs (digital data) produced by the AD converter 18 of the light receiver 14 during a predetermined time period.

Next, the peak bottom detector 22 detects a peak value and a bottom value of changes in the transmitted light signal L1 stored in the storage device 20A and corresponding to the wavelength λ1, so that time points at which the peak value and the bottom value appear (hereinafter, referred as a peak time point and a bottom time point). The peak bottom detector 22 is configured such that a peak time point and a bottom time point can be detected arbitrarily even though changes in the transmitted light signal L1 are non-periodic; e.g., even when disturbed by body motion.

Accordingly, the respective attenuation change calculators 24A to 24E of the first calculator 24 captures the transmitted light signals of the respective wavelengths at the peak and bottom time points which have been obtained by the peak bottom detector 22. In this case, the peak and bottom time points are both past times, and values of transmitted light at the time points are represented as L1(t-t0), L2(t-t0), L3(t-t0), L4(t-t0), and L5(t-t0) (t0 denotes a time in the past). The respective attenuation change calculators 24A to 24E calculate the attenuation changes ΔAi corresponding to the peak and bottom time points with the following approximations:

$$\Delta Ai = \frac{Li(tp) - Li(tb)}{Li}$$

where, i=1, 2, 3, 4, 5; tp denotes the peak time point; and tb denotes the bottom time point.

From the attenuation changes ΔAi obtained by the respective attenuation change calculators 24A to 24E of the first calculator 24, ratios between the attenuation changes Φij are obtained from the following equations:

Φ12=ΔA1/ΔA2

Φ34=ΔA3/ΔA4

Φ51=ΔA5/ΔA1

Φ23=ΔA2/ΔA3

Φ45=ΔA4/ΔA5

In this case, the respective attenuation changes are represented by the following theoretical formulae:

$$\Phi 12 = \frac{\Delta A1}{\Delta A2} = \frac{Eba1 + Ebv1V + W}{Eba2 + Ebv2V + B2 + W} \quad (1)$$

$$\Phi 34 = \frac{\Delta A3}{\Delta A4} = \frac{Eba3 + Ebv3V + W}{Eba4 + Ebv4V + W} \quad (2)$$

$$\Phi 51 = \frac{\Delta A5}{\Delta A1} = \frac{Eba5 + Ebv5V + W}{Eba1 + Ebv1V + W} \quad (3)$$

$$\Phi 23 = \frac{\Delta A2}{\Delta A3} = \frac{Eba2 + Ebv2V + B2 + W}{Eba3 + Ebv3V + W} \quad (4)$$

$$\Phi 45 = \frac{\Delta A4}{\Delta A5} = \frac{Eba4 + Ebv4V + W}{Eba5 + Ebv5V + W} \quad (5)$$

where, $$Ebai = \sqrt{[SaEoi + (1-Sa)Eri] \cdot [SaEoi + (1-Sa)Eri + F]}$$
$$Ebvi = \sqrt{[SvEoi + (1-Sv)Eri] \cdot [SvEoi + (1-Sv)Eri + F]}$$

Sa denotes an oxygen saturation of arterial blood; Sv denotes an oxygen saturation of venous blood; Eo denotes an extinction coefficient of oxyhemoglobin; Er denotes an extinction coefficient of deoxyhemoglobin; F denotes a scattering coefficient; and V denotes a ratio of the amplitude of a change in arterial blood ΔDv to the amplitude of a change in venous blood ΔDa, that is, ΔDv/ΔDa.

W denotes changes in living tissue. Comparison of actual data and theoretical formulae on a certain probe has revealed that W has a slight wavelength dependency. In view of the dependency, "W+B2" is used instead of W for the second wavelength.

When W is eliminated from the equations (1) to (5), the following equations hold:

$$\frac{\Phi 12(Eba2+B2+Ebv2V) - (Eba1+Ebv1V)}{\theta 12} = \frac{\Phi 34(Eba4+Ebv4V) - (Eba3+Ebv3V)}{\theta 34} \quad (6)$$

$$\frac{\Phi 34(Eba4+Ebv4V) - (Eba3+Ebv3V)}{\theta 34} = \frac{\Phi 51(Eba1+Ebv1V) - (Eba5+Ebv5V)}{\theta 51} \quad (7)$$

$$\frac{\Phi 51(Eba1+Ebv1V) - (Eba5+Ebv5V)}{\theta 51} = \frac{\Phi 23(Eba3+Ebv3V) - (Eba2+B2+Ebv2V)}{\theta 23} \quad (8)$$

$$\frac{\Phi 23(Eba3+Ebv3V) - (Eba2+B2+Ebv2V)}{\theta 23} = \frac{\Phi 45(Eba5+Ebv5V) - (Eba4+Ebv4V)}{\theta 45} \quad (9)$$

where, $\theta ij = (1-\Phi ij)$.

Subsequently, when V is eliminated from the above equations, the following nonlinear simultaneous equations with two unknowns (10) and (11) can be obtained.

$$\frac{[\Phi 12(Eba2+B2) - Eba1]/\theta 12 - (\Phi 34Eba4 - Eba3)/\theta 34}{(\Phi 12Ebv2 - Ebv1)/\theta 12 - (\Phi 34Ebv4 - Ebv3)/\theta 34} = \frac{(\Phi 34Eba4 - Eba3)/\theta 34 - (\Phi 51Eba1 - Eba5)/\theta 51}{(\Phi 34Ebv4 - Ebv3)/\theta 34 - (\Phi 51Ebv1 - Ebv5)/\theta 51} \quad (10)$$

$$\frac{[\Phi 23Eba3 - (Eba2+B2)]/\theta 23 - (\Phi 51Eba1 - Eba5)/\theta 51}{(\Phi 51Ebv1 - Ebv5)/\theta 51 - (\Phi 23Ebv3 - Ebv2)/\theta 23} = \frac{(\Phi 45Eba5 - Eba4)/\theta 45 - [\Phi 23Eba3 - (Eba2+B2)]/\theta 23}{(\Phi 23Ebv3 - Ebv2)/\theta 23 - (\Phi 45Ebv5 - Ebv4)/\theta 45} \quad (11)$$

Here, the following approximations are made:
Eba1=(A13Eba3+B13);
Eba2=(A23Eba3+B23);
Eba4=(A43Eba3+B43);
Eba5=(A53Eba3+B53);
Ebv1=(A13Ebv3+B13);
Ebv2=(A23Ebv3+B23);
Ebv4=(A43Ebv3+B43);
Ebv5=(A53Ebv3+B53);

When these approximations are substituted into equations (10) and (11), equations (10) and (11) are transformed into simultaneous linear equations with two unknowns for Eba3. When Ebv3 is eliminated from the equation, the following linear equation for Eba3 is obtained:

$$Eba3 = \frac{(NL-JP)/(NI-JM) - F(B+D)/(FA-BE)}{(AF+ED)/(FA-BE) - (ML-IP)/(NI-JM)} \quad (12)$$

where,
A: $(\Phi 34A43-1)/\theta 34 - (\Phi 12A23-A13)/\theta 12$;
B: $\Phi 34B43/\theta 34 - [\Phi 12(B23+B) - B13]/\theta 12$;
D: $(\Phi 12B23-B13)/\theta 12 - \Phi 34B43/\theta 34$;
E: $(\Phi 51A13-A53)/\theta 51 - (\Phi 34A43-1)/\theta 34$;
F: $(\Phi 51B13-B53)/\theta 51 - \Phi 34B43/\theta 34$;
I: $(\Phi 23-A23)/\theta 23 - (\Phi 51A13-A53)/\theta 51$;
J: $-(B23+B)/\theta 23 - (\Phi 51B13-B53)/\theta 51$;
L: $(\Phi 51B13-B53)/\theta 51 + B23/\theta 23$;
M: $(\Phi 45A53-A43)/\theta 45 - (\Phi 23-A23)/\theta 23$;
N: $(\Phi 45B53-B43)/\theta 45 + (B23+B)/\theta 23$; and
P: $-B23/\theta 23 - (\Phi 45B53-B43)/\theta 45$.

Furthermore, details of the above definitions are as follows:
A13: [Eb1(0.8)−Eb1(1)]/[Eb3(0.8)−Eb3(1)];
A23: [Eb2(0.8)−Eb2(1)]/[Eb3(0.8)−Eb3(1)];
A43: [Eb4(0.8)−Eb4(1)]/[Eb3(0.8)−Eb3(1)];
A53: [Eb5(0.8)−Eb5(1)]/[Eb3(0.8)−Eb3(1)];
B13: −A13Eb3(1)+Eb1(1);
B23: −A23Eb3(1)+Eb2(1);
B43: −A43Eb3(1)+Eb4(1); and
B53: −A53Eb3(1)+Eb5(1).

Meanwhile, Ebi(0.8) and Ebi(1) denote constants; Ebi(0.8) is a value of Ebi where an oxygen saturation is 0.8, and Ebi(1) is a value of Ebi where an oxygen saturation is 1.

Next, Eba3 is converted into an oxygen saturation of arterial blood by the following equation:

$$Sa = \frac{-B - \sqrt{B^3 - 4AC}}{2A} \quad (13)$$

where,

A: $(Eo3-Er3)^2$

B: $(Eo3-Er3)(2Er3+F)$

C: $Er3(F+Er3)-Eba3^2$

Application of the above equations provides a pulse oximeter which eliminates the influence of artifacts stemming from body motion so as to obtain an oxygen saturation of arterial blood with high precision on the basis of transmitted light of five wavelengths through living tissue.

In the first calculator 24, the respective attenuation change calculators 24A to 24E execute calculating operations of the attenuation changes ΔAi on the basis of the aforementioned calculating operations.

Further, calculating operations of Eba3 and Sa are executed in the second calculator 26 based on the above equations (12) and (13).

An example operation of the pulse oximeter configured as described above will be described below.

The following five wavelengths were used: λ1=805 nm; λ2=875 nm; λ3=660 nm; λ4=700 nm; and λ5=730 nm. Meanwhile, with regard to a single point of original data, λ2 and λ3 were used for a two-wavelength calculation, and λ1, λ2, and λ3 were used for a three-wavelength calculation. A subject shook his/her hand from the wrist strongly as body motion while wearing a probe attached to the tip of his/her finger, whereby artifact characteristics of the motion were determined respectively.

Figure 2:
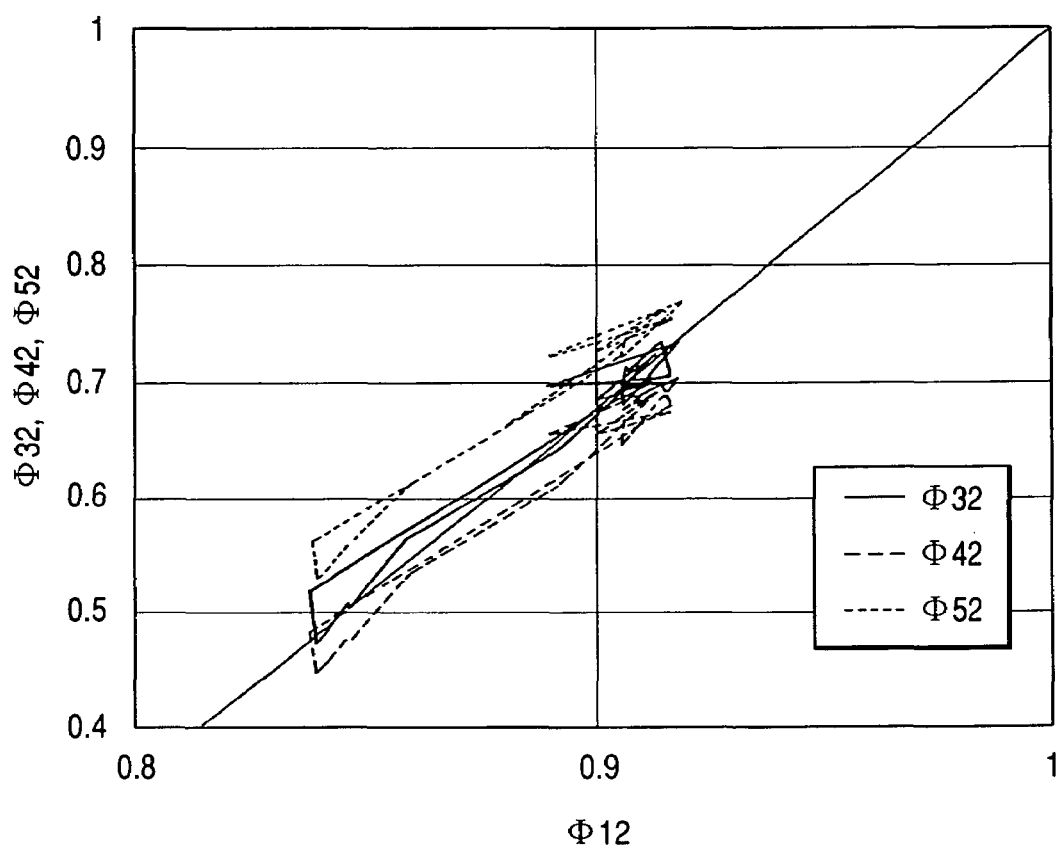
FIG. 2 is a graph showing a trace on Φ—Φ planes in a case where a subject moved his hand in a "waving" manner.
Figure 3A:
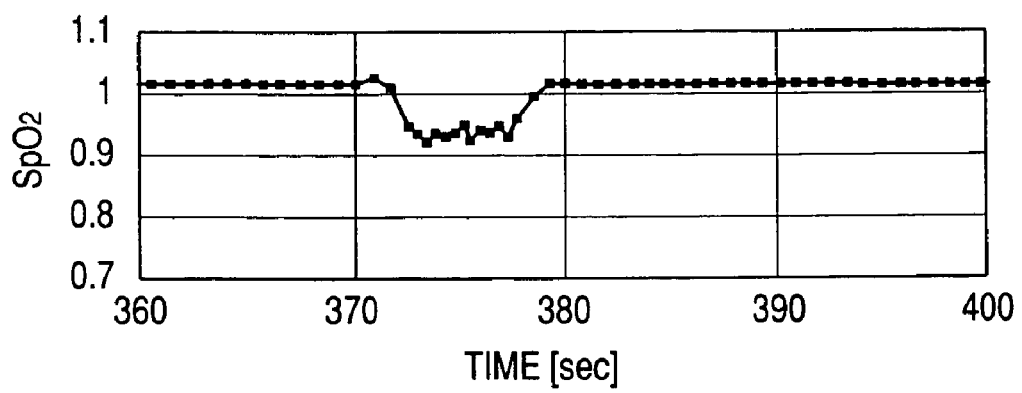
FIG. 3A is a graph showing artifact characteristics obtained by a two-wavelength calculation as a result of body motion in the case of FIG. 2.
Figure 3B:
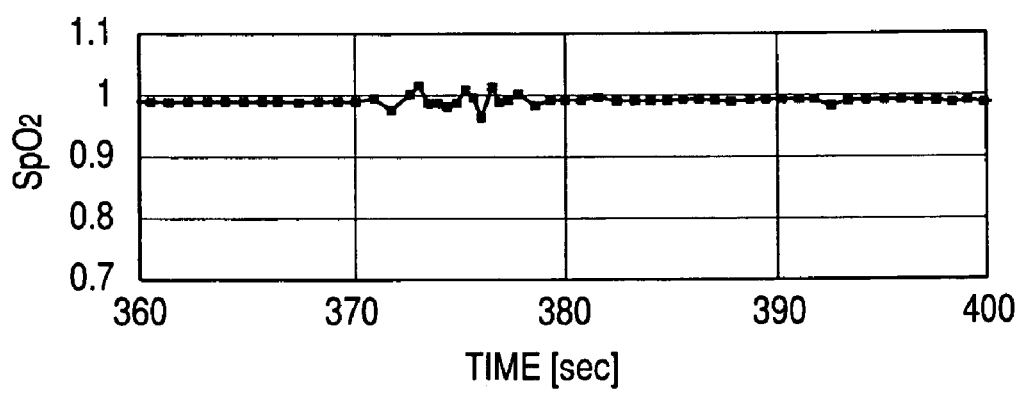
FIG. 3B is a graph showing artifact characteristics obtained by a three-wavelength calculation as a result of body motion in the case of FIG. 2.
Figure 3C:
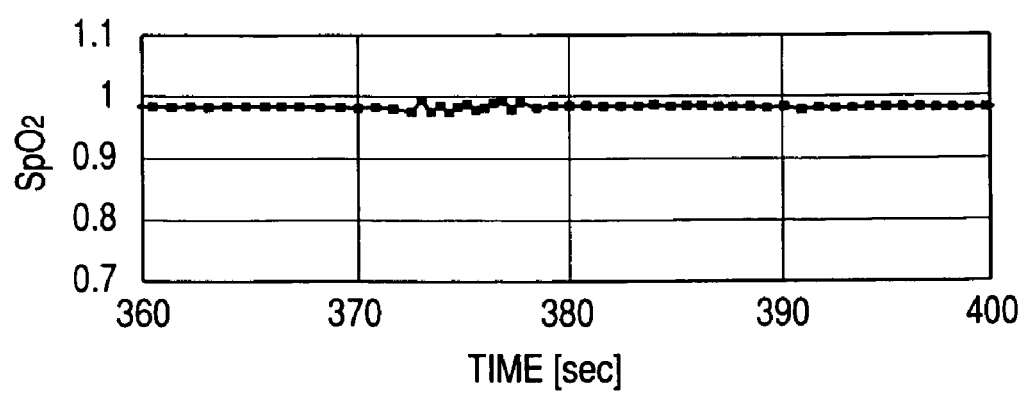
FIG. 3C is a graph showing artifact characteristics obtained by a five-wavelength calculation as a result of body motion in the case of FIG. 2.

The subject moved his/her hand in a "waving" manner. Specifically, the subject lies on a bed in a supine position such that his/her arm extends downward over the edge of the bed. The subject shakes the hand in the front and back motion while the palm is directed backward (i.e., waving). FIG. 2 shows a trace on Φ—Φ planes as results of the body motion. These changes show artifacts mainly stemming from changes of tissue. FIG. 3A shows artifact characteristics obtained by a two-wavelength calculation which indicates large artifacts. FIG. 3B shows artifact characteristics obtained by a three-wavelength calculation which indicates that most of the artifacts are eliminated. FIG. 3C shows artifact characteristics obtained by a five-wavelength calculation which indicates that artifacts are further reduced.

Figure 4:
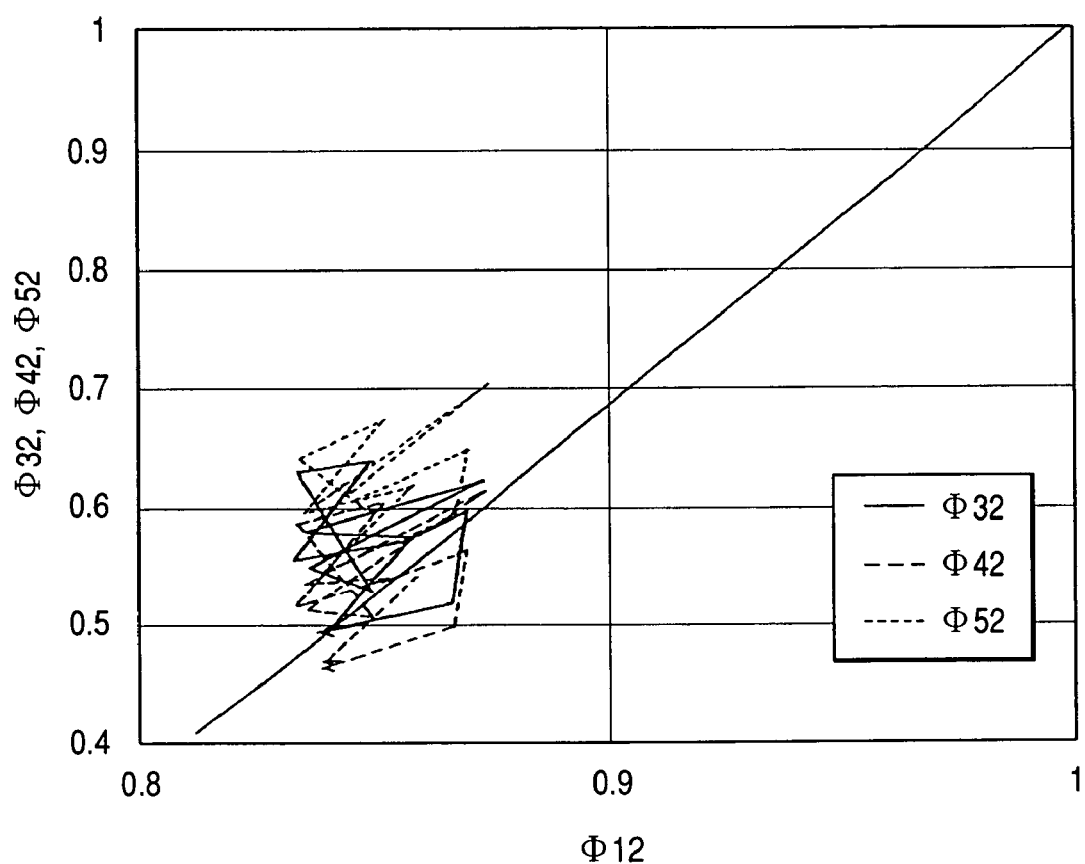
FIG. 4 is a graph showing a trace on Φ—Φ planes in a case where a subject moved his hand in a "chopping" manner.
Figure 5A:
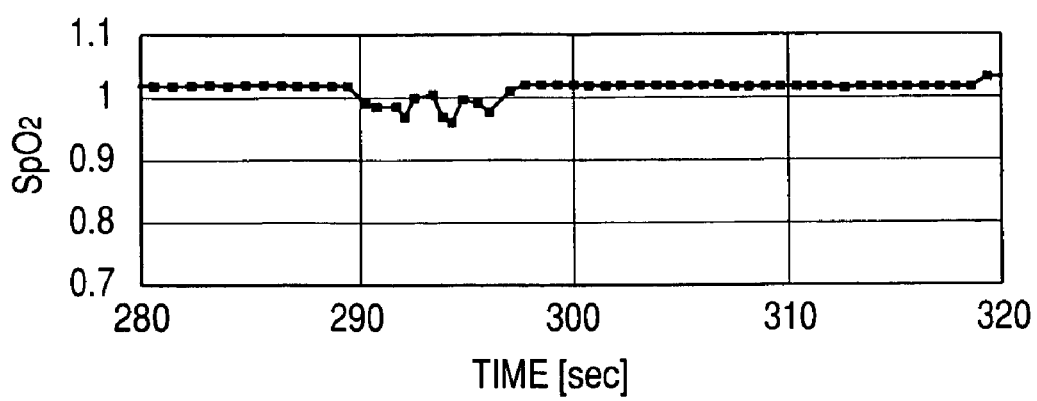
FIG. 5A is a graph showing artifact characteristics obtained by the two-wavelength calculation as a result of body motion in the case of FIG. 4.
Figure 5B:
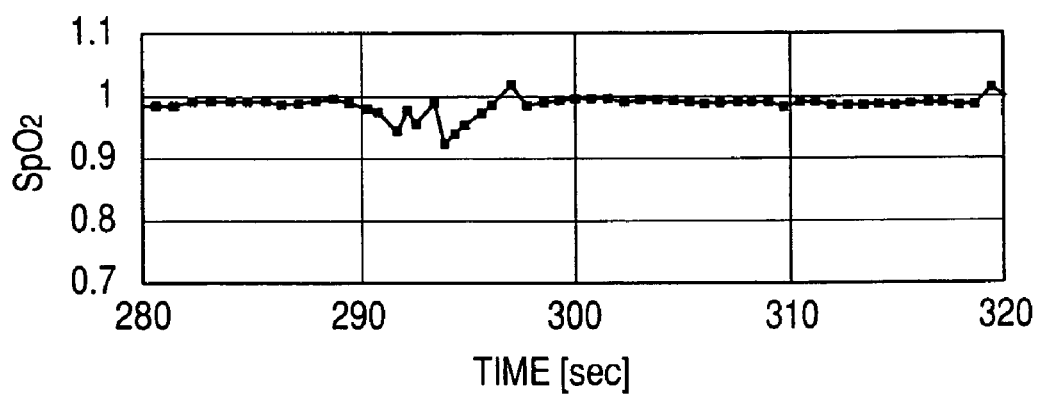
FIG. 5B is a graph showing artifact characteristics obtained by the three-wavelength calculation as a result of body motion in the case of FIG. 4.
Figure 5C:
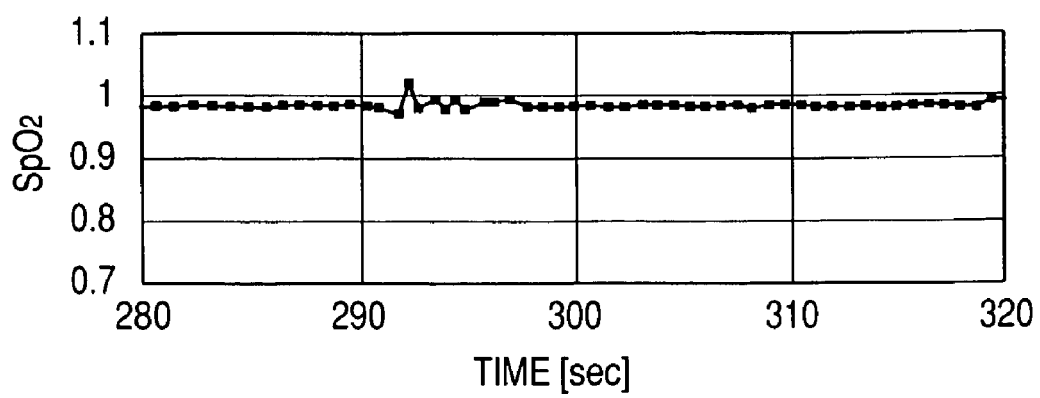
FIG. 5C is a graph showing artifact characteristics obtained by the five-wavelength calculation as a result of body motion in the case of FIG. 4.

Further, the subject moved his/her hand in a "chopping" manner. Specifically, the subject lies on a bed in a supine position such that his/her arm extends parallel to the side of the body on the bed. The subject shakes the hand in the up and down motion while the palm is directed inward (i.e., chopping). FIG. 4 shows a trace on Φ—Φ planes as results of the body motion. FIG. 5A shows artifact characteristics obtained by the two-wavelength calculation which indicates large artifacts. FIG. 5B shows artifact characteristics obtained by the three-wavelength calculation which indicates slight improvement in artifacts. FIG. 5C shows artifact characteristics obtained by the five-wavelength calculation which indicates that most of the artifacts are eliminated.

Figure 6A:
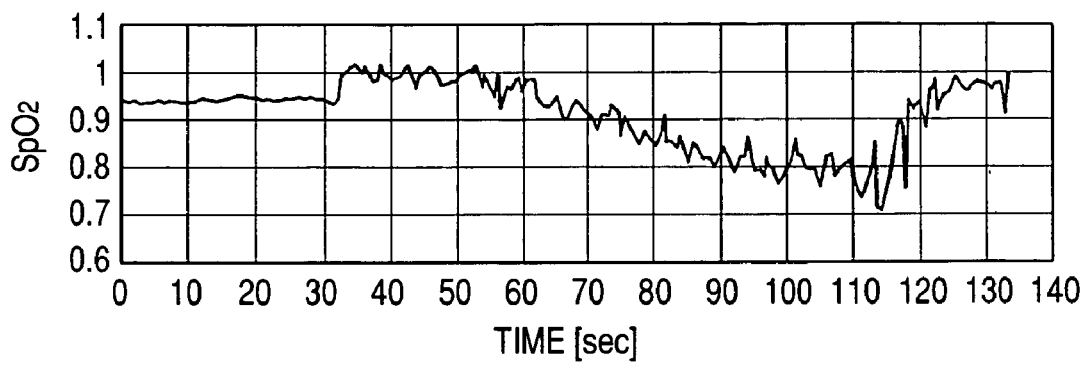
FIG. 6A is a graph showing artifact characteristics obtained by the two-wavelength calculation in a case where a subject moved his hand in the "waving" manner after holding his breath.
Figure 6B:
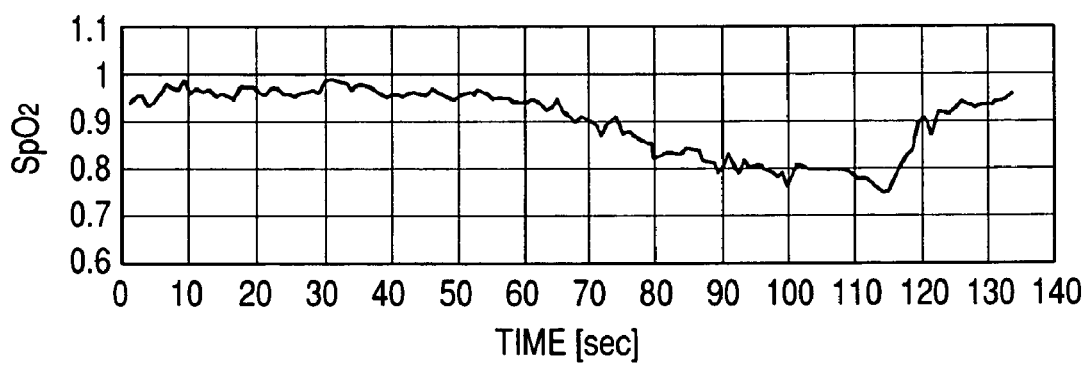
FIG. 6B is a graph showing artifact characteristics obtained by the three-wavelength calculation as a result of body motion in the case of FIG. 6A.
Figure 6C:
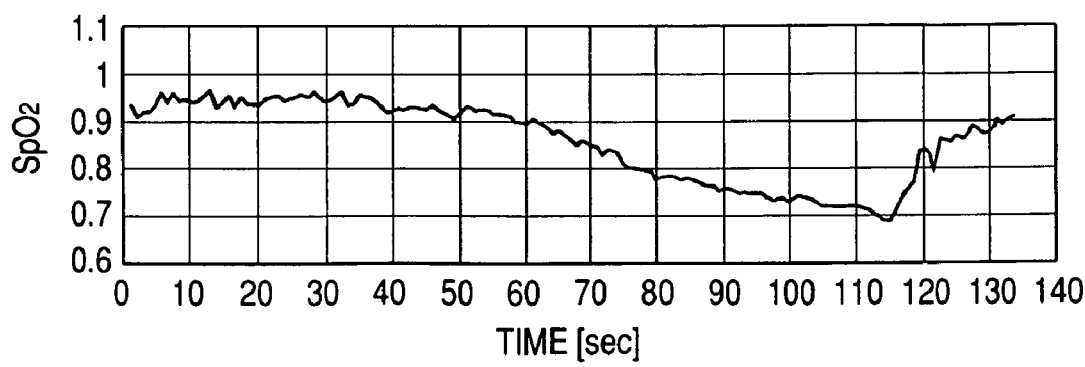
FIG. 6C is a graph showing artifact characteristics obtained by the five-wavelength calculation as a result of body motion in the case of FIG. 6A.

FIGS. 6A to 6C show artifact characteristics obtained in a case where the subject started moving his/her hand in the "waving" manner, after about 30 seconds from the start of measurement in a state where oxygen saturation of arterial blood had been lowered by holding his breath. FIG. 6A show artifact characteristics obtained by the two-wavelength calculation which indicates relatively large artifacts. FIG. 6B shows artifact characteristics obtained by the three-wavelength calculation which indicates improvements with respect to artifacts. FIG. 6C shows artifact characteristics obtained by the five-wavelength calculation which indicates further improvements with respect to artifacts.

Meanwhile, in this case, attenuation changes ΔAi have a wide range of magnitude during periods of the artifacts. Therefore; attenuation changes of a predetermined level or lower have been removed in calculations. Such processing is simple and has been applied to numerous pulse oximeters. Accordingly, detailed descriptions of the processing will be omitted.

Figure 7A:
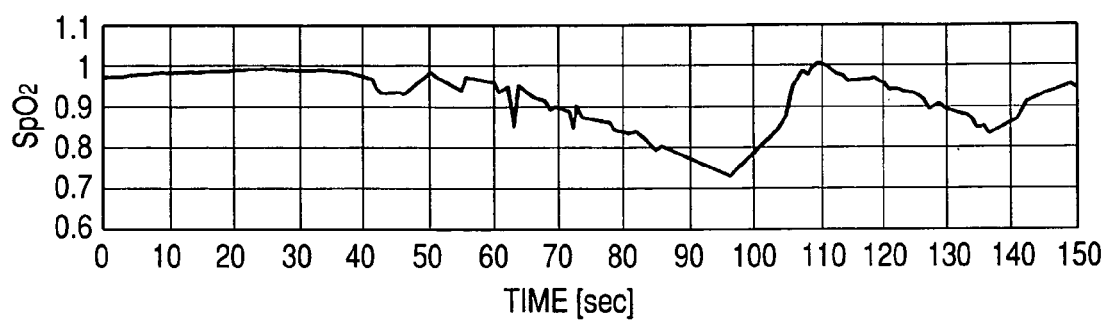
FIG. 7A is a graph showing artifact characteristics obtained by the two-wavelength calculation in a case where a subject moved his hand in the "chopping" manner after holding his breath.
Figure 7B:
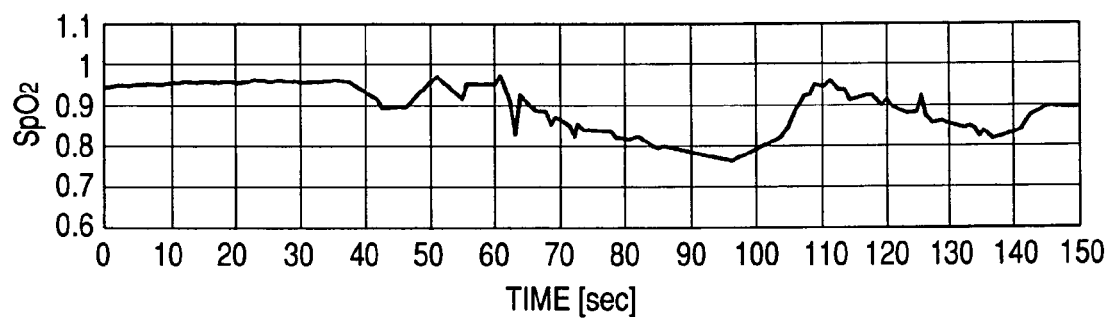
FIG. 7B is a graph showing artifact characteristics obtained by the three-wavelength calculation as a result of body motion in the case of FIG. 7A.
Figure 7C:
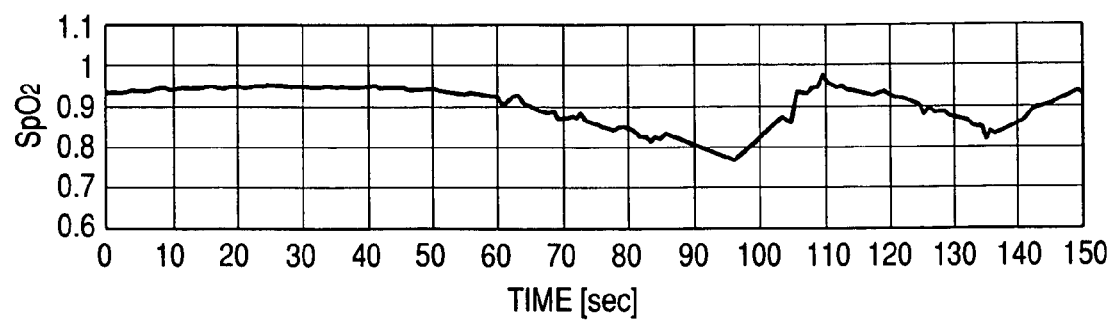
FIG. 7C is a graph showing artifact characteristics obtained by the five-wavelength calculation as a result of body motion in the case of FIG. 7A.

FIGS. 7A to 7C show artifact characteristics obtained in a case where the subject started moving his/her hand in the "chopping" manner, after about 30 seconds from the start of measurement in a state where oxygen saturation of arterial blood had been lowered by holding his breath. FIG. 7A shows artifact characteristics obtained by the two-wavelength calculation which indicates relatively large artifacts. FIG. 7B shows artifact characteristics obtained by the three-wavelength calculation which Indicates little improvement in artifacts. FIG. 7C shows artifact characteristics obtained by the five-wavelength calculation which indicates that most of the artifacts are eliminated.

Even in a case where a pulse wave in a living tissue of a subject is so small that a pulse oximetry is not applicable, according to the invention, measurement of an oxygen saturation of arterial blood is enabled by forcibly causing body motion against the living tissue by a vibration mechanism or the like, to thus generate artifacts on attenuation changes in a light signal transmitted through the living tissue.

In addition, simultaneously with the oxygen saturation of arterial blood, an oxygen saturation of venous blood can also be measured.

The preferred embodiment of the invention has been described; however, it should be understood that the present invention is not limited to the embodiment, and may be modified in various manners without departing from the scope of the invention.

What is claimed is:

1. A pulse oximeter for obtaining an oxygen saturation in blood, comprising:

a light emitter, adapted to irradiate a living tissue with light beams having five different wavelengths;

a light receiver, adapted to receive respective light beams reflected from or transmitted through the living tissue, and to convert the received light beams to electric signals;

a first calculator, operable to calculate five attenuation changes of the living tissue based on fluctuations of the respective electric signals;

a second calculator, operable to calculate four attenuation change ratios from the five attenuation changes, each of the attenuation change ratios being defined by a ratio between any two of the five attenuation changes; and a third calculator, operable to establish four simultaneous equations each of which is associated with one of the four attenuation change ratios and takes an oxygen saturation of arterial blood, an oxygen saturation of venous blood, a ratio between changes in arterial blood and venous blood, and a tissue term as four unknown values, the third calculator operable to solve the simultaneous equations by eliminating the oxygen saturation of venous blood, the ratio between changes in arterial blood and venous blood, and the tissue term in order to obtain the oxygen saturation in arterial blood.

2. The pulse oximeter as set forth in claim 1, wherein;

the four simultaneous equations are four of the following equations:

$$\Phi 12 = \frac{\Delta A1}{\Delta A2} = \frac{Eba1 + Ebv1V + W}{Eba2 + Ebv2V + B2 + W};$$

$$\Phi 34 = \frac{\Delta A3}{\Delta A4} = \frac{Eba3 + Ebv3V + W}{Eba4 + Ebv4V + W};$$

$$\Phi 51 = \frac{\Delta A5}{\Delta A1} = \frac{Eba5 + Ebv5V + W}{Eba1 + Ebv1V + W};$$

$$\Phi 23 = \frac{\Delta A2}{\Delta A3} = \frac{Eba2 + Ebv2V + B2 + W}{Eba3 + Ebv3V + W}; \text{ and}$$

$$\Phi 45 = \frac{\Delta A4}{\Delta A5} = \frac{Eba4 + Ebv4V + W}{Eba5 + Ebv5V + W},$$

where, $$Ebai = \sqrt{[SaEoi + (1 - Sa)Eri] \cdot [SaEoi + (1 - Sa)Eri + F]};$$

$$Ebvi = \sqrt{[SvEoi + (1 - Sv)Eri] \cdot [SvEoi + (1 - Sv)Eri + F]}:$$

Sa denotes an oxygen saturation of arterial blood;
Sv denotes an oxygen saturation of venous blood;
Eo denotes an extinction coefficient of oxyhemoglobin;
Er denotes an extinction coefficient of deoxyhemoglobin;
F denotes a scattering coefficient;
V denotes a ratio of the amplitude of a change in arterial blood to the amplitude of a change in venous blood; and
W denotes changes in living tissue.

3. A method of obtaining an oxygen saturation signal for use in indicating an oxygen saturation in blood, comprising:

placing a light emitter and a light receiver on a living tissue in a non-invasive manner;
irradiating the living tissue with light beams emitted from the light emitter and having five different wavelengths;
receiving respective light beams reflected from or transmitted through the living tissue by the light receiver;
converting the received light beams to electric signals;
calculating five attenuation changes of the living tissue based on fluctuations of the respective electric signals;
calculating four attenuation change ratios from the five attenuation changes, each of the attenuation change ratios being defined by a ratio between any two of the five attenuation changes;
establishing four simultaneous equations each of which is associated with one of the four attenuation change ratios and takes an oxygen saturation of arterial blood, an oxygen saturation of venous blood, a ratio between changes in arterial blood and venous blood, and a tissue term as four unknown values;
solving the simultaneous equations by eliminating the oxygen saturation of venous blood, the ratio between changes in arterial blood and venous blood, and the tissue term in order to obtain the oxygen saturation in arterial blood; and
generating the oxygen saturation signal based on the obtained oxygen saturation of arterial blood.

4. The method as set forth in claim 3, wherein;
the four simultaneous equations are four of the following equations:

$$\Phi 12 = \frac{\Delta A1}{\Delta A2} = \frac{Eba1 + Ebv1V + W}{Eba2 + Ebv2V + B2 + W};$$

$$\Phi 34 = \frac{\Delta A3}{\Delta A4} = \frac{Eba3 + Ebv3V + W}{Eba4 + Ebv4V + W};$$

$$\Phi 51 = \frac{\Delta A5}{\Delta A1} = \frac{Eba5 + Ebv5V + W}{Eba1 + Ebv1V + W};$$

$$\Phi 23 = \frac{\Delta A2}{\Delta A3} = \frac{Eba2 + Ebv2V + B2 + W}{Eba3 + Ebv3V + W}; \text{ and}$$

$$\Phi 45 = \frac{\Delta A4}{\Delta A5} = \frac{Eba4 + Ebv4V + W}{Eba5 + Ebv5V + W},$$

where, $$Ebai = \sqrt{[SaEoi + (1-Sa)Eri] \cdot [SaEoi + (1-Sa)Eri + F]};$$
$$Ebvi = \sqrt{[SvEoi + (1-Sv)Eri] \cdot [SvEoi + (1-Sv)Eri + F]}:$$

Sa denotes an oxygen saturation of arterial blood;
Sv denotes an oxygen saturation of venous blood;
Eo denotes an extinction coefficient of oxyhemoglobin;
Er denotes an extinction coefficient of deoxyhemoglobin;
F denotes a scattering coefficient;
V denotes a ratio of the amplitude of a change in arterial blood to the amplitude of a change in venous blood; and
W denotes changes in living tissue.

* * * * *